(12) United States Patent
White et al.

(10) Patent No.: US 6,713,052 B1
(45) Date of Patent: Mar. 30, 2004

(54) METHOD OF MOBILIZING STEM CELLS WITH CHEMOKINE β-8

(75) Inventors: John R. White, Coatsville, PA (US); Louis Pelus, Richboro, PA (US); Haodong Li, Germantown, MD (US); Brendt L. Kreider, Germantown, MD (US)

(73) Assignees: Human Genome Sciences, Inc., Rockville, MD (US); SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/567,225

(22) Filed: May 9, 2000

Related U.S. Application Data

(60) Continuation of application No. 09/225,501, filed on Jan. 6, 1999, now abandoned, which is a division of application No. 08/740,033, filed on Oct. 23, 1996, now abandoned.
(60) Provisional application No. 60/006,051, filed on Oct. 24, 1995.

(51) Int. Cl.$^7$ ............................................... A61K 38/19
(52) U.S. Cl. ............................. 424/85.1; 514/2; 514/8; 514/12; 930/140
(58) Field of Search .............................. 435/69.5, 71.1, 435/71.2, 325; 424/85.1; 536/23.1, 23.5; 530/300, 351; 930/140; 514/2, 8, 12

(56) References Cited

U.S. PATENT DOCUMENTS

| 5,556,767 A | 9/1996 | Rosen et al. ............... 435/69.1 |
| 5,602,008 A | 2/1997 | Wilde et al. ............... 435/69.5 |
| 6,001,606 A | 12/1999 | Ruben et al. ............. 435/69.5 |
| 6,290,948 B1 | 9/2001 | White et al. .............. 424/85.1 |
| 2002/0007047 A1 | 1/2002 | White et al. ............... 530/351 |

FOREIGN PATENT DOCUMENTS

| WO | WO 94/28916 | 12/1994 |
| WO | WO 95/17092 | 6/1995 |
| WO | WO 95/18228 | 7/1995 |

OTHER PUBLICATIONS

Drize, N. et al., "Effect of recombinant human granulocyte colony–stimulating factor treatment of mice on spleen colony–forming unit number and self–renewal capacity," *Exp. Hematol.* 21:1289–1293, International Society for Experimental Hematology (1993).

Haas, R. et al., "Successful Autologous Transplantation of Blood Stem Cells Mobilized with Recombinant Human Granulocyte–Macrophage Colony–stimulating Factor," *Exp. Hematol.* 18:94–98, International Society for Experimental Hematology (1990).

Richman, C.M. et al., "Increase in Circulating Stem Cells Following Chemotherapy in Man," *Blood 47:* 1031–1039, Grune & Stratton, Inc. (1976).

van der Ham, A.C. et al., "Mobilization of B and T Lymphocytes and Haemopoietic Stem Cells by Polymethacrylic Acid and Dextran Sulphate," *Cell Tissue Kinet.* 10:387–397, Blackwell Scientific Publications (1977).

Zander, A.R. et al., "Pyran Copolymer: Effect of Molecular Weight on Stem Cell Mobilization in Mice," *Biomedicine* 33:69–72, Masson Publishing USA, Inc. (1980).

Cullen et al. (1989) *Endocrinology* 125(4);1774–1782.

Baggliolini, M. And Sorg, C., eds., Interleukin–8 (NAP–1) and Related Chemotactic Cytokines in *Cytokines*, vol. 4, 1992.

Brugger et al. (1992) *Blood* 79(5):1193–1200.

Clore et al. (1995) *FASEB J.* 9:57–62.

Graves et al. (1995) *Crit. Rev. Oral Biol. Med.* 6(2):109–118.

Horuk, R. (1994) *Trends Pharmacol. Sci.* 15:159–165.

Laterveer et al. (1995) *Blood* 85(8):2269–2275.

Taub et al. (1993) *Cytokine* 5(3):175–179.

Gencore Accession No. R76128 (Dec.–2–1995) Hillier et al.
Gencore Accession No. R77600 (Mar.–5–1996) Hillier et al.

*Primary Examiner*—Prema Mertz
(74) *Attorney, Agent, or Firm*—Human Genome Sciences, Inc.

(57) ABSTRACT

Novel chemokines for mobilizing stem cells are provided. Methods of mobilizing stem cells are also provided.

21 Claims, 1 Drawing Sheet

FIGURE 1

| | | | |
|---|---|---|---|
| hRANTES | | ASPYSSDT | TPCCFAYIARPLPRAHIKEYFYTSGK CSNPAVVFVTRKNRQVC ANPEKKWVREYINSLEMS |
| hMIP-1α | | APYGADTPTACCFSY | SRKIPRQFIVDYFETSSL CSQKAVIFLTKRNRQIC ADSKETWVQEYITDLELNA |
| hMIP-1β | | APMGSDPPTSCCFSY | TSRQLHRSFVMDYYETSSL CSKPAVVFLTKRGRQIC ANPSEPWVTEYMSDLELN |
| MCP-1 | | | LAQPDAINAPVTCCYNFTNRKISVQRLASYRRITSSK CTKRAVIFKTIVAKEI CADPKQKWVQDSMDHLDKQTQTPKT |
| MCP-3 | | SPQGLAQPVGINTSTTCCYRFINKKIPKQRLESYRRTTSSH CPREAVIFKTKLDKEIC ADPTQKWVQDFMKHLDKKTQTPKL |
| CKβ-1 | | TKTESSSRGPYHPSECCFTYTTYKIPRQRIMDYYETNSQ CSKPGIVFITKRGHSV CTNPSDKWVQDYIKDMK |
| CKβ-4 | | ASNFDCCLGYTDRILHPKFIVGFTRQLANEGCDINAIIFHTKKKLSV CANPKQTWVKYIVRLLSKKVKNM |
| CKβ-6 | | VVIPSPCCMFFVSKRIPENRVVSYQLSSRST CLKGGVIFTTKRGQQF CGDPKQEMVQRYMKNLDAKQKKA |
| CKβ-7 | | AQVGTNKELCCLCVTSWQIFQKFIVDYSETSPQ CPKPGVILLTKRGRQI CADPNKKWVQK |
| CKβ-8 | | ENPVLLDRFHATSADCCISYTPRSIPCSLLESYFETNSE CSKPGVIFLTKRGRRF CANPSDKQVQVCMRMLKLDTRIKTRKN |
| CKβ-9 | | SDAGGAQDCCLKYSQKIPAKVVRSYRKQEPSLGCSIPAILPLPRKRSQAEL CADPKELWVQQLMQHILDKTPSPQKPAQ |
| CKβ-10 | | FNPQGLAQPDALNVPSTCCFTESSKKISLQRLKSYVITTSR CPQKAVIFKTKLGKEI CADPKEKWVQNYMKHLGRKAHTLKT |
| CKβ-11 | | PAPTLSGTNDAEDCCLSVTQKPIPGYIVRNFHYLLIKDGCRVPAVVFTTLRGRQL CAPPDQPWVERIIQRLQRTSAKMKRRSS |
| CKβ-12 | | RSQPKVPEWVNTPSTCCLKYYEKVLPRRLVGYRKALN CHLPAIIFVTKRNREV CTNPNDDWVQEYIKDPNLPLLPTRNLST |
| CKβ-13 | | PYGANMEDSVCCRDYVRYRLPLRVVKHFYWTSDS CPRPGVVLLTKRDKHI CADPRVPWVKMILNKLSQ |

| | |
|---|---|
| NAP-1/IL-8 | SAKELRCQCIKTYSKPFHPKFIKELRVIESGPHCANTEIIVKLSDGRELCLDPKENWVQRVVEKFLKRAENS |
| NAP-2 | AELRCMCIKTTSGIHPKNIQSLEVIGKGTHCNQVEVIATLKDGRKICLDPDAPRIKKIVQKKLAGDESAD |
| hPF4 | EAEEDGDLQCLCVKTTSQVRPRHITSLEVIKAGPH CPTAQLIATLKNGRKICLDLQAFLYKKLLKKLES |
| CKα-1 | VLEVYYTSLRCRCVQESSVFIPRRFIDRIQILPRGNGCPRKELIVKKNKSIVCVDPQAEWIQRMMEVLRKR |

```
                           SEQUENCE LISTING

<160> NUMBER OF SEQ ID NOS:   19

<210> SEQ ID NO 1
<211> LENGTH: 72
<212> TYPE: PRT
<213> ORGANISM: CKBeta-1

<400> SEQUENCE: 1

Thr Lys Thr Glu Ser Ser Arg Gly Pro Tyr His Pro Ser Glu Cys
1               5                   10                  15

Cys Phe Thr Tyr Thr Thr Tyr Lys Ile Pro Arg Gln Arg Ile Met Asp
                20                  25                  30

Tyr Tyr Glu Thr Asn Ser Gln Cys Ser Lys Pro Gly Ile Val Phe Ile
                35                  40                  45

Thr Lys Arg Gly His Ser Val Cys Thr Asn Pro Ser Asp Lys Trp Val
        50                  55                  60

Gln Asp Tyr Ile Lys Asp Met Lys
65                  70

<210> SEQ ID NO 2
<211> LENGTH: 70
<212> TYPE: PRT
<213> ORGANISM: CKBeta-4

<400> SEQUENCE: 2

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
                20                  25                  30

Asp Ile Asn Ala Ile Ile Phe His Thr Lys Lys Lys Leu Ser Val Cys
                35                  40                  45

Ala Asn Pro Lys Gln Thr Trp Val Lys Tyr Ile Val Arg Leu Leu Ser
        50                  55                  60

Lys Lys Val Lys Asn Met
65                  70

<210> SEQ ID NO 3
<211> LENGTH: 70
<212> TYPE: PRT
<213> ORGANISM: CKBeta-6

<400> SEQUENCE: 3

Val Val Ile Pro Ser Pro Cys Cys Met Phe Phe Val Ser Lys Arg Ile
1               5                   10                  15

Pro Glu Asn Arg Val Val Ser Tyr Gln Leu Ser Ser Arg Ser Thr Cys
                20                  25                  30

Leu Lys Gly Gly Val Ile Phe Thr Thr Lys Lys Gly Gln Gln Phe Cys
                35                  40                  45

Gly Asp Pro Lys Gln Glu Trp Val Gln Arg Tyr Met Lys Asn Leu Asp
        50                  55                  60

Ala Lys Gln Lys Lys Ala
65                  70
```

```
<210> SEQ ID NO 4
<211> LENGTH: 60
<212> TYPE: PRT
<213> ORGANISM: CKBeta-7

<400> SEQUENCE: 4

Ala Gln Val Gly Thr Asn Lys Glu Leu Cys Cys Leu Val Tyr Thr Ser
1               5                   10                  15

Trp Gln Ile Pro Gln Lys Phe Ile Val Asp Tyr Ser Glu Thr Ser Pro
            20                  25                  30

Gln Cys Pro Lys Pro Gly Val Ile Leu Leu Thr Lys Arg Gly Arg Gln
        35                  40                  45

Ile Cys Ala Asp Pro Asn Lys Lys Trp Val Gln Lys
    50                  55                  60

<210> SEQ ID NO 5
<211> LENGTH: 82
<212> TYPE: PRT
<213> ORGANISM: CKBeta-8

<400> SEQUENCE: 5

Glu Asn Pro Val Leu Leu Asp Arg Phe His Ala Thr Ser Ala Asp Cys
1               5                   10                  15

Cys Ile Ser Tyr Thr Pro Arg Ser Ile Pro Cys Ser Leu Leu Glu Ser
            20                  25                  30

Tyr Phe Glu Thr Asn Ser Glu Cys Ser Lys Pro Gly Val Ile Phe Leu
        35                  40                  45

Thr Lys Lys Gly Arg Arg Phe Cys Ala Asn Pro Ser Asp Lys Gln Val
    50                  55                  60

Gln Val Cys Met Arg Met Leu Lys Leu Asp Thr Arg Ile Lys Thr Arg
65                  70                  75                  80

Lys Asn

<210> SEQ ID NO 6
<211> LENGTH: 79
<212> TYPE: PRT
<213> ORGANISM: CKBeta-9

<400> SEQUENCE: 6

Ser Asp Ala Gly Gly Ala Gln Asp Cys Cys Leu Lys Tyr Ser Gln Arg
1               5                   10                  15

Lys Ile Pro Ala Lys Val Val Arg Ser Tyr Arg Lys Gln Glu Pro Ser
            20                  25                  30

Leu Gly Cys Ser Ile Pro Ala Ile Leu Phe Leu Pro Arg Lys Arg Ser
        35                  40                  45

Gln Ala Glu Leu Cys Ala Asp Pro Lys Glu Leu Trp Val Gln Gln Leu
    50                  55                  60

Met Gln His Leu Asp Lys Thr Pro Ser Pro Gln Lys Pro Ala Gln
65                  70                  75

<210> SEQ ID NO 7
<211> LENGTH: 82
<212> TYPE: PRT
<213> ORGANISM: CKBeta-10

<400> SEQUENCE: 7

Phe Asn Pro Gln Gly Leu Ala Gln Pro Asp Ala Leu Asn Val Pro Ser
1               5                   10                  15
```

-continued

Thr Cys Cys Phe Thr Phe Ser Ser Lys Lys Ile Ser Leu Gln Arg Leu
                20                  25                  30

Lys Ser Tyr Val Ile Thr Thr Ser Arg Cys Pro Gln Lys Ala Val Ile
            35                  40                  45

Phe Arg Thr Lys Leu Gly Lys Glu Ile Cys Ala Asp Pro Lys Glu Lys
 50                  55                  60

Trp Val Gln Asn Tyr Met Lys His Leu Gly Arg Lys Ala His Thr Leu
 65                  70                  75                  80

Lys Thr

<210> SEQ ID NO 8
<211> LENGTH: 83
<212> TYPE: PRT
<213> ORGANISM: CKBeta-11

<400> SEQUENCE: 8

Pro Ala Pro Thr Leu Ser Gly Thr Asn Asp Ala Glu Asp Cys Cys Leu
 1               5                  10                  15

Ser Val Thr Gln Lys Pro Ile Pro Gly Tyr Ile Val Arg Asn Phe His
                20                  25                  30

Tyr Leu Leu Ile Lys Asp Gly Cys Arg Val Pro Ala Val Val Phe Thr
            35                  40                  45

Thr Leu Arg Gly Arg Gln Leu Cys Ala Pro Pro Asp Gln Pro Trp Val
 50                  55                  60

Glu Arg Ile Ile Gln Arg Leu Gln Arg Thr Ser Ala Lys Met Lys Arg
 65                  70                  75                  80

Arg Ser Ser

<210> SEQ ID NO 9
<211> LENGTH: 82
<212> TYPE: PRT
<213> ORGANISM: CKBeta-12

<400> SEQUENCE: 9

Arg Ser Gln Pro Lys Val Pro Glu Trp Val Asn Thr Pro Ser Thr Cys
 1               5                  10                  15

Cys Leu Lys Tyr Tyr Glu Lys Val Leu Pro Arg Arg Leu Val Val Gly
                20                  25                  30

Tyr Arg Lys Ala Leu Asn Cys His Leu Pro Ala Ile Ile Phe Val Thr
            35                  40                  45

Lys Arg Asn Arg Glu Val Cys Thr Asn Pro Asn Asp Asp Trp Val Gln
 50                  55                  60

Glu Tyr Ile Lys Asp Pro Asn Leu Pro Leu Leu Pro Thr Arg Asn Leu
 65                  70                  75                  80

Ser Thr

<210> SEQ ID NO 10
<211> LENGTH: 68
<212> TYPE: PRT
<213> ORGANISM: CKBeta-13

<400> SEQUENCE: 10

Pro Tyr Gly Ala Asn Met Glu Asp Ser Val Cys Cys Arg Asp Tyr Val
 1               5                  10                  15

Arg Tyr Arg Leu Pro Leu Arg Val Val Lys His Phe Tyr Trp Thr Ser
                20                  25                  30

Asp Ser Cys Pro Arg Pro Gly Val Val Leu Leu Thr Phe Arg Asp Lys

```
                35                  40                  45
Glu Ile Cys Ala Asp Pro Arg Val Pro Trp Val Lys Met Ile Leu Asn
            50                  55                  60
Lys Leu Ser Gln
65
```

<210> SEQ ID NO 11
<211> LENGTH: 69
<212> TYPE: PRT
<213> ORGANISM: hRANTES

<400> SEQUENCE: 11

```
Ala Ser Pro Tyr Ser Ser Asp Thr Thr Pro Cys Cys Phe Ala Tyr Ile
1               5                   10                  15
Ala Arg Pro Leu Pro Arg Ala His Ile Lys Glu Tyr Phe Tyr Thr Ser
            20                  25                  30
Gly Lys Cys Ser Asn Pro Ala Val Val Phe Val Thr Arg Lys Asn Arg
            35                  40                  45
Gln Val Cys Ala Asn Pro Glu Lys Lys Trp Val Arg Glu Tyr Ile Asn
            50                  55                  60
Ser Leu Glu Met Ser
65
```

<210> SEQ ID NO 12
<211> LENGTH: 69
<212> TYPE: PRT
<213> ORGANISM: mMIP-1alpha

<400> SEQUENCE: 12

```
Ala Pro Tyr Gly Ala Asp Thr Pro Thr Ala Cys Cys Phe Ser Tyr Ser
1               5                   10                  15
Arg Lys Ile Pro Arg Gln Phe Ile Val Asp Tyr Phe Glu Thr Ser Ser
            20                  25                  30
Leu Cys Ser Gln Pro Gly Val Ile Phe Leu Thr Lys Arg Asn Arg Gln
            35                  40                  45
Ile Cys Ala Asp Ser Lys Glu Thr Trp Val Gln Glu Tyr Ile Thr Asp
            50                  55                  60
Leu Glu Leu Asn Ala
65
```

<210> SEQ ID NO 13
<211> LENGTH: 69
<212> TYPE: PRT
<213> ORGANISM: mMIP-1beta

<400> SEQUENCE: 13

```
Ala Pro Met Gly Ser Asp Pro Pro Thr Ser Cys Cys Phe Ser Tyr Thr
1               5                   10                  15
Ser Arg Gln Leu His Arg Ser Phe Val Met Asp Tyr Tyr Glu Thr Ser
            20                  25                  30
Ser Leu Cys Ser Lys Pro Ala Val Val Phe Leu Thr Lys Arg Gly Arg
            35                  40                  45
Gln Ile Cys Ala Asn Pro Ser Glu Pro Trp Val Thr Glu Tyr Met Ser
            50                  55                  60
Asp Leu Glu Leu Asn
65
```

<210> SEQ ID NO 14

```
<211> LENGTH: 78
<212> TYPE: PRT
<213> ORGANISM: MCP-1

<400> SEQUENCE: 14

Leu Ala Gln Pro Asp Ala Ile Asn Ala Pro Val Thr Cys Cys Tyr Asn
1               5                   10                  15

Phe Thr Asn Arg Lys Ile Ser Val Gln Arg Leu Ala Ser Tyr Arg Arg
            20                  25                  30

Ile Thr Ser Ser Lys Cys Pro Lys Glu Ala Val Ile Phe Lys Thr Ile
            35                  40                  45

Val Ala Lys Glu Ile Cys Ala Asp Pro Lys Gln Lys Trp Val Gln Asp
        50                  55                  60

Ser Met Asp His Leu Asp Lys Gln Thr Gln Thr Pro Lys Thr
65                  70                  75

<210> SEQ ID NO 15
<211> LENGTH: 82
<212> TYPE: PRT
<213> ORGANISM: MCP-3

<400> SEQUENCE: 15

Ser Pro Gln Gly Leu Ala Gln Pro Val Gly Ile Asn Thr Ser Thr Thr
1               5                   10                  15

Cys Cys Tyr Arg Phe Ile Asn Lys Lys Ile Pro Lys Gln Arg Leu Glu
            20                  25                  30

Ser Tyr Arg Arg Thr Thr Ser Ser His Cys Pro Arg Glu Ala Val Ile
            35                  40                  45

Phe Lys Thr Lys Leu Asp Lys Glu Ile Cys Ala Asp Pro Thr Gln Lys
        50                  55                  60

Trp Val Gln Asp Phe Met Lys His Leu Asp Lys Lys Thr Gln Thr Pro
65                  70                  75                  80

Lys Leu

<210> SEQ ID NO 16
<211> LENGTH: 72
<212> TYPE: PRT
<213> ORGANISM: NAP-1/IL-8

<400> SEQUENCE: 16

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70

<210> SEQ ID NO 17
<211> LENGTH: 71
<212> TYPE: PRT
<213> ORGANISM: NAP-2

<400> SEQUENCE: 17

Ala Glu Leu Arg Cys Met Cys Ile Lys Thr Thr Ser Gly Ile His Pro
1               5                   10                  15
```

```
Lys Asn Ile Gln Ser Leu Glu Val Val Ile Gly Lys Gly Thr His Cys
            20                  25                  30

Asn Gln Val Glu Val Ile Ala Thr Leu Lys Asp Gly Arg Lys Ile Cys
            35                  40                  45

Leu Asp Pro Asp Ala Pro Arg Ile Lys Lys Ile Val Gln Lys Lys Leu
            50                  55                  60

Ala Gly Asp Glu Ser Ala Asp
65                  70

<210> SEQ ID NO 18
<211> LENGTH: 69
<212> TYPE: PRT
<213> ORGANISM: hPF4

<400> SEQUENCE: 18

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
            35                  40                  45

Arg Lys Ile Cys Leu Asp Leu Gln Ala Pro Leu Tyr Lys Lys Ile Leu
            50                  55                  60

Lys Lys Leu Glu Ser
65

<210> SEQ ID NO 19
<211> LENGTH: 72
<212> TYPE: PRT
<213> ORGANISM: CKApha-1

<400> SEQUENCE: 19

Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30

Pro Arg Gly Asn Gly Cys Pro Arg Lys Glu Ile Ile Val Trp Lys Lys
            35                  40                  45

Asn Lys Ser Ile Val Cys Val Asp Pro Gln Ala Glu Trp Ile Gln Arg
            50                  55                  60

Met Met Glu Val Leu Arg Lys Arg
65                  70
```

METHOD OF MOBILIZING STEM CELLS WITH CHEMOKINE β-8

This application is a continuation of and claims priority under 35 U.S.C § 120, to U.S. patent application No. 09/225,501, filed Jan. 6, 1999 now abandoned, which is a divisional of U.S. patent application No. 08/740,033, filed Oct. 23, 1996 now abandoned, which claims priority under 35 U.S.C. § 119(e) to U.S. Provisional Patent Application Ser. No: 60/006,051, filed Oct. 24, 1995, all herein incorporated by reference in their entirety.

BACKGROUND OF THE INVENTION

Hematopoietic cells have very important roles in a number of different processes in the body. For example, leukocytic hematopoietic cells are important in maintaining the body's defenses against disease; monocytes, macrophages and lymphocytes are involved in potentiating the body's responses to infection and tumors, while granulocytes are involved in overcoming infection, parasites and tumors. Platelets, another hematopoietic cell, form an important element in the hemostatic mechanism through initiating thrombus formation by their adhesion to each other and to damaged surfaces, and by the release to factors which assist in the formation of the fibrin clot. Erythrocytes are mainly involved in the transport of oxygen.

All of these blood cells are derived from a single progenitor cell called the hematopoietic stem cell. Stem cells are both pluripotent, in that they give rise to all different cell types, and capable of self renewal. Hematopoietic stem cells make up only a small percentage of bone marrow cells and are normally quiescent. However, when stimulated to divide, these stem cells produce a differentiated daughter cell with great proliferative potential. Sequential rounds of division and differentiation give rise to an enormous amplification of cell numbers which is necessary for the production of mature blood cells. This process of division and differentiation is subject to regulation at many levels to control cell production.

Numerous studies have led to the definition of functions of several hematopoietic regulatory messengers. These biomolecules have been characterized as stimulatory, e.g., Colony Stimulating Factors (CSFs) and interleukins (IL-1, IL-3, IL-5 and IL-9); inhibitory, e.g., transforming growth factor-β, (TGF-β), interferon, prostaglandin E, tumor necrosis factor, macrophage inflammatory protein-1 (MIP-1), lactoferrin, acidic isoferritins, AcSKDP, and pEEDCK (a synthetic HP5B monomer); or enhancing, e.g., TGF-β, IL-6, IL-4, IL-9, IL-11, MIP-1, MIP-2, leukemia inhibitory factor and Steel factor. Pelus et al. Experimental Hematology 1994, 22:239–247. Stimulatory biomolecules have been found to promote division of particular cell lineages. For examine, G-CSF derives neutrophil production, while erythropoietin promotes formation of erythrocytes.

A number of these biomolecules and additional agents have been found to induce the mobilization of hematopoietic stem cells.

A single injection of IL-8 has been shown to induce mobilization of pluripotent stem cells that are able to provide permanent reconstitution of myeloid cells and of T and B lymphocytes. Later-veer et al. Blood 1995, 85(8) :2269–2275. IL-8 belongs to a family of pro-inflammatory molecules called chemokines. This family has been divided into two subfamilies, the CXC and CC chemokines, based on whether the first two cysteine residues in a conserved motif are adjacent to each other or are separated by an intervening residue. In general, CXC, which include IL-8, melanoma growth-stimulating activity (MGSA) and platelet factor 4 (PF4), are potent chemoattractants and activators of neutrophils but not monocytes. In contrast, CC chemokines, which include RANTES, monocyte chemotactic protein 1 (MCP-1) and MIP-1, are chemoattractants for monocytes but not neutrophils.

Stem cell inhibitors (SCIs) such as the CC chemokines, murine and human MIP-1α (LD78), have also been shown to enhance the release and mobilization of cells into the peripheral blood. WO 94/28916; Simm et al. Blood 1994, 84:2937.

Increased mobilization of stem cells in patients treated with sequentially administered interleukin-3 and GM-CSF compared with GM-CSF alone has been reported by Brugger et al. Blood 1992, 79:1193–1200. In addition, it has been shown that the absolute number of peripheral blood progenitor cells can be expanded in vitro by culture in a cocktail of cytokines, usually including SCF, IL-3, and either IL-6 or IL-1. Bodine, D. Experimental Hematology 1995, 23:293–295.

SK&F 107647, a hematoregulatory agent containing an ethylene bridge in place of the cysteine bridge of HP5B, has been demonstrated to be a potent stimulator of in vitro myelopoiesis. Pelus et al. Experimental Hematology 1994, 22:239–247. Injection of SK&F 107647 in normal mice resulted in a two- to six-fold increase in serum colony-stimulating activity. Administration of this agent over 4 days resulted in significant increases in the number of granulocyte-macrophage, erythroid, and multipotential progenitor cells, as well as stimulating their cell cycle rates.

It has also been found that pretreatment with stem cell stimulating factor such as G-CSF can expand the pool of progenitor cells susceptible for mobilization by these agents, further increasing their mobilizing effect. For example, the combination of MIP-1α with G-CSF was found to increase white cell count in the blood as compared to G-CSF alone. Simm et al. Blood 1994, 84:2937. Co-administration of SCI with G-CSF caused the enhanced mobilization of a number of cell types including neutrophils, monocytes, eosinphils, lymphocytes and basophils. WO 94/28916. Administration of G-CSF alone had no effect on the release of eosinphils or basophils after 2 days of administration. Similar effects were observed when other agents such as GM-CSF, f-MET-Leu-Phe or IL-8 were coadministered with SCIs.

New chemokines have now been identified which also mobilize stem cells in an animal. These chemokines can be administered alone, or in combination with a colony stimulating factor or hemoregulatory agent to enhance mobilization of stem cells.

SUMMARY OF THE INVENTION

An object of the present invention is to provide novel chemokines for the mobilization of stem cells in an animal.

Another object of the invention is to provide a method of mobilizing stem cells.

BRIEF DESCRIPTION OF THE DRAWINGS

FIG. 1 shows the sequence and alignment of the novel chemokines with known chemokines.

DETAILED DESCRIPTION OF THE INVENTION

In recent years, the availability of recombinant cytokines and the use of hematopoietic stem cell support have resulted in the widespread application of high-dose chemotherapy regimens designed to improve the success of cancer therapy. Despite significant advances, however, delayed recovery of hematopoiesis remains an important source of morbidity and mortality for patients treated with this approach. Since their discovery over 20 years ago, peripheral blood hematopoietic progenitor cells (PBPCs) have been increasingly used to supplement and even replace bone marrow as the source of hematopoietic support in a variety of situations.

Purified populations of cells are increasingly being used therapeutically and it would therefore be advantageous to be able to increase the number of circulating blood cells. It is useful to be able to harvest hematopoietic cells prior to chemotherapy or radiotherapy, thus, protecting them from harmful effects of this therapy; after therapy, the cells can be returned to the patient. It would therefore be highly beneficial to provide an agent which promoted the release and mobilization of a number of hematopoietic cells. Such an agent would be useful for enhancing the response to infection.

Peripheral blood cell transplantation is an important procedure in the treatment of cancer patients with high dose chemotherapy. In such treatment, patients are treated to induce clinical remission of their cancer, then during the remission, successive treatment with CSF, for example, by priming with cyclophosphamide then administration of G-CSF, causes eventual mobilization of cells from the bone marrow to the peripheral circulation for harvesting of leukophoresed blood; then the patient is given high dose chemotherapy or radiotherapy and the resultant bone marrow failure is compensated for by infusion of the stored blood or cells collected previously. This procedure may be modified by the omission of the initial induction of remission, and whole blood may be collected rather than leukophoresed blood. The mobilization effects of the present invention makes it a candidate both to replace CSFs in such cancer treatment regimes, and also to complement the mobilization effects of CSFs in combined treatments.

The two subfamilies of chemokines (CXC and CC) are ever expanding and presumably the individual members have similar, if slightly divergent, function. The chemokines disclosed in the present invention are new members of the CC subfamily and are structurally similar to MCP-1, MCP-3, hRANTES, mMIP-1α,and mMIP-1β (FIG. 1). The effect of these chemokines in inducing leukophilia will find clinical and veterinary application in all utilities where the raising of hematopoietic cell levels is important. For example, a chemokine of the present invention can be used to enhance immune responses against chronic infections, particularly parasitic and bacterial infections. It may also have a role in promoting wound healing.

The chemoattractant activity of these chemokines can be boosted by pretreatment with a colony stimulating factor such as G-CSF or GM-CSF. Alternatively, the hematoregulatory peptides SK&F 107647 (currently in clinical trials), FLT-3 ligand (Immunex) or any other G-CSF mimetics (peptide and non-peptide) may be used. These stimulants may have an even more dramatic effect on these novel chemokines than on those already known due to their slight structural differences. For example, CKB-6 in combination with G-CSF was effective as a mobilizing factor. As known in the art, these peptides are useful in stimulating myelopoiesis in patients suffering from reduced myelopoietic activity, including bone marrow damage, agranulocytosis and aplastic anemia. Also included are patients who have depressed bone marrow function due to immunosuppressive treatment to suppress tissue reactions (i.e., bone marrow transplant surgery). They may also be used to promote more rapid regeneration of bone marrow after cytostatic chemotherapy and radiation therapy for neoplastic and viral diseases. There may also be a value where patients have serious infections due to a lack of immune response following bone marrow failure.

The hematopoietic stem cells released and harvested in the manner described above may be useful for subsequent in vitro and ex vivo manipulations to deliver gene products in gene therapy. Another embodiment is co-administration with cytotoxic drugs.

The following examples are provided for illustrative purposes only and are not intended to limit the invention.

EXAMPLES

Example 1

Mobilization Assay for Novel Chemokines as Single Agents

A panel of novel chemokines will be tested as individual stem cell mobilization agents in BDF 1 mice. These chemokines include, but should not be limited to: Ckβ-1, Ckβ-4, Ckβ-6, Ckβ,-7, Ckβ-8, Ckβ-9, Ckβ-10, Ckβ-11, Ckβ-12, Ckβ-13, and Ckα-1. Each agent will be assayed in concentrations of 50, 10, and 2 μg/mouse and administered via SC, IM, or a PO route. The kinetics of chemokine mobilization of stem cells will be monitored in 15 minute intervals over a period of 60 minutes by collecting blood samples from the mice by cardiac puncture. The mobilized stem cells will be collected by a densing gradient (Lympholyte M). Cells are washed then frozen for future usage. The mobilization profile of the blood differentials will be assessed using a Technicon H1 hematology analyzer. Mobilization of inflammatory cells such as PMN's, eosinophils, and basophils will be taken into account when evaluating the overall potential inflammatory profile. The chemokine IL-8, which mobilizes hematopoietic stem cells as a single factor, will be included in these studies as a positive control.

Example 2

Mobilization Assay for Novel Chemokines in Combination with Hematostimulants

In these studies, hematostimulants will be assayed in combination with the aforementioned chemokines as mobilization factors. These agents include: G-CSF, GM-CSF, SK&F 107647, and FLT-3 ligand. However, any G-CSF mimetic (hematostimulants which are not colony stimulating factors like G-CSF or GMCSF, but have hematopoietic activity) may be used. In combination studies, G-CSF will be administered IP to mice four days prior to the novel chemokines. As in Example 1, the dose of chemokine and time of blood collection will be varied. Combination studies with hematostimulant pre-treatment will utilize MIP-1α as the positive control.

Example 3

CFU Assay

Blood samples collected during the mobilization phase will be assessed for colony forming units (CFU-GM) at days 7 and 14. Cells are adjusted to $2\times10^6$ cells/ml in McCoys medium with 15×FBS serum. A single layer agar system utilizing the following is used: McCoys medium enriched with nutrients (NaHCO3, pyruvate, amino acids and vitamins); 0.3% Bacto agar. To this is added cells from the blood samples (final concentration=2×10$^5$ cells/ml). The agar plates are incubated at 37° C., 5% CO2 for 7 days. Colonies of proliferating cells (CFU-GM) are counted utilizing a microscope. In addition, early hematopoietic high proliferative potential (HPP) progenitors, will be counted in the day 14 CFU cultures.

What is claimed is:

1. A method of mobilizing hematopoietic stem cells in an animal having need of cancer therapy, comprising:
   (a) administering to said animal an effective amount of a polypeptide comprising SEQ ID NO:5; and
   (b) thereby inducing the mobilization of said hematopoietic stem cells.

2. The method of claim 1, further comprising administering to said animal a cytotoxic drug.

3. The method of claim 1, further comprising administering to said animal a colony stimulating factor.

4. The method of claim 1, further comprising administering to said animal an agent that stimulates or enhances hematopoiesis.

5. The method of claim 1, wherein said animal is a human.

6. The method of claim 1, wherein said animal is undergoing cancer therapy.

7. The method of claim 6, wherein said cancer therapy is chemotherapy.

8. The method of claim 6, wherein said cancer therapy is radiation therapy.

9. The method of claim 6, wherein said polypeptide is administered prior to said cancer therapy.

10. The method of claim 9, further comprising administering to said animal a colony stimulating factor.

11. The method of claim 9, further comprising administering to said animal an agent that stimulates or enhances hematopoiesis.

12. The method of claim 9, wherein said animal is a human.

13. The method of claim 9, further comprising collecting hematopoietic stem cells which have been mobilized from said animal, prior to administration of said cancer therapy.

14. The method of claim 13; further comprising administering said collected hematopoietic stem cells to said animal, after administration of said cancer therapy.

15. The method of claim 6, wherein said polypeptide is administered to said animal after said cancer therapy.

16. The method of claim 15, further comprising administering to said animal a colony stimulating factor.

17. The method of claim 15, further comprising administering to said animal an agent that stimulates or enhances hematopoiesis.

18. The method of claim 15, wherein said animal is a human.

19. The method of claim 15, further comprising collecting hematopoietic stem cells which have been mobilized from said animal.

20. The method of claim 19, further comprising administering additional cancer therapy to said animal after said stem cell collection.

21. The method of claim 20, further comprising administering said collected hematopoietic stem cells to said animal, after said administration of additional cancer therapy.

* * * * *